United States Patent
Gupta et al.

(10) Patent No.: US 10,563,181 B2
(45) Date of Patent: Feb. 18, 2020

(54) **MOLECULAR CLONING AND EXPRESSION OF CDNA ENCODING O-METHYLTRANSFERASE ISOLATED FROM *MANGIFERA INDICA***

(71) Applicant: COUNCIL OF SCIENTIFIC & INDUSTRIAL RESEARCH, New Delhi (IN)

(72) Inventors: Vidya Shrikant Gupta, Pune (IN); Hemangi Girish Chidley, Pune (IN); Ashish Balwant Deshpande, Pune (IN); Ashok Prabhakar Giri, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 155 days.

(21) Appl. No.: 15/737,729

(22) PCT Filed: Jun. 16, 2016

(86) PCT No.: PCT/IN2016/050184
§ 371 (c)(1),
(2) Date: Dec. 18, 2017

(87) PCT Pub. No.: WO2016/203494
PCT Pub. Date: Dec. 22, 2016

(65) Prior Publication Data
US 2018/0179498 A1 Jun. 28, 2018

(30) Foreign Application Priority Data
Jun. 16, 2015 (IN) .......................... 1795/DEL/2015

(51) Int. Cl.
*C12N 9/10* (2006.01)
*C12P 7/22* (2006.01)
*C12P 7/24* (2006.01)
*C12P 7/42* (2006.01)
*C12P 17/04* (2006.01)

(52) U.S. Cl.
CPC .............. *C12N 9/1007* (2013.01); *C12P 7/22* (2013.01); *C12P 7/24* (2013.01); *C12P 7/42* (2013.01); *C12P 17/04* (2013.01)

(58) Field of Classification Search
CPC .......... C12N 9/1007; C12P 17/04; C12P 7/22; C12P 7/24; C12P 7/42
See application file for complete search history.

(56) References Cited

FOREIGN PATENT DOCUMENTS

WO 2013114407 A2 8/2013

OTHER PUBLICATIONS

Barghini, P., et al., "Optimal conditions for bioconversion of ferulic acid into vanillic acid by Pseudomonas fluorescens BF13 cells", Appl Microbiol Biotechnol 49:309-314 (1998).

Chidley, Hemangi G., et al., "Spatial and temporal changes in the volatile profile of Alphonso mango upon exogenous ethylene treatment", Food Chemistry 136:585-594 (2013).
Kulkarni, Ram S., et al., "Geographic variation in the flavour volatiles of Alphonso mango", Food Chemistry 130:58-66 (2010).
MacLeod, Alexander J. and Nirmala M. Pieris, "Comparison of the volatile components of some mango cultivars", Phytochemistry 23(2):361-366 (1984) ScienceDirect—Phytochemistry: Comparison of the volatile components . . . http://www.sciencedirect.com/science?_ob=ArticleURL&_udi=B6TH7 . . . .
Mukherjee, K.S., and R.E. Litz, "The Mango: Botany, Production and Uses", 2nd Edition, Richard E. Litz, ed., CAB International 2009.
Pandit, Sagar S., et al., "Cultivar relationships in mango based on fruit volatile profiles", Food Chemistry 114:363-372 (2009).
Pandit, Sagar S., et al., "Changes in volatile composition during fruit development and ripening of "Alphonso" mango", J. Sci Food Agri 89:2071-2081 (2009).
Pino, Jorge A., et al., "Volatile Components from Mango (*Mangifera indica* L.) Cultivars", J. Agric. Food Chem. 53:2213-2223 (2005).
Pino, Jorge A. and Judith Mesa, "Contribution of volatile compounds to mango (*Mangifera indica* L.) aroma", Flavour and Fragrance Journal 21:207-213 (2006).
Priefert, H., et al., "Biotechnological production of vanillin", Appl. Microbiol. Biotechnol. 56:296-314 (2001).
Sakho, M., et al., "African Mango Glycosidically Bound Volatile Compounds", J. Agric. Food Chem 45:883-888 (1997).
Kaur, Surinder, et al., "Water Biomass: A Prospective Renewal Resource for Development of Bio-Based Economy/Processes", Chapter 1, pp. 1-26 from "Biotransformation of Waste Biomass into High Value Biochemicals", S. K. Brar et al., Eds. Springer Science + Business Media, New York 2014.
Schwab, Wilfried, "Natural 4-Hydroxy-2,5-dimethyl-3(2H)-furanone (Furaneol®)", Molecules 18:6936-6951 (2013), www.mdpi.com/journal/molecules.
Wein, Martina, et al., "Isolation, cloning and expression of a multifunctional O-methyltransferase capable of forming 2,5-dimethyl-4-methoxy-3(2H)-furanone, one of the key aroma compounds in strawberry fruits", The Plant Journal, 31 (6):755-765 (2002).
Wilson, Charles W., et al., "Importance of Some Lactones and 2,5-Dimethoyl -4-hydroxy-3(2H)-furanone to Mango (*Mangifera indica* L.) Aroma", J. Agric. Food Chem. 38:1556-1559 (1990).
Kulkarni, Ram, et al., "An oxidoreductase from "Alphonso" mango catalyzing biosynthesis of furaneaol and reduction of reactive carbonyls", Springerplus, (2013) 2(1):494.

(Continued)

*Primary Examiner* — Kagnew H Gebreyesus
(74) *Attorney, Agent, or Firm* — Melissa M. Hayworth; E. Joseph Gess

(57) ABSTRACT

The present invention relates to the cloning and expression of cDNA encoding O-methyl transferase for catalyzing the synthesis of vital volatile flavor compounds such as mesifuran and vanillin, thereby playing a significant role in flavor biochemistry of mango. The present invention also provide a process for the preparation of volatile compounds by mesifuran, ferulic acid, guaiacol and vanillin, specifically mesifuran and vanillin using cDNA sequence.

14 Claims, 6 Drawing Sheets
Specification includes a Sequence Listing.

(56) References Cited

OTHER PUBLICATIONS

Lavid, Noa, et al., "Aroma Biosynthesis in Strawberry: S-Adenosylmethionine: Furaneaol O-Methyltransferase Activity in Ripening Fruits", J. Agric. Food Chem. (2002) 50: 4025-4030.
Pino, Jorge A. and Judith Mesa, "Contribution of volatile compounds to mango (*Mangifera indica L.*) aroma", Flavour and Fragrance Journal (2006) 21: 207-213.
Frick, Susanne and Toni M. Kutchan, "Molecular cloning and functional expression of O-methyltransferases common to isoquinoline alkaloid and phenylpropanoid biosynthesis" The Plant Journal (1999) 17(4): 329-339.
Pandit, Sagar S., et al., "Cultivar relationships in mango based on fruit volatile profiles", Food Chemistry (2009) 114: 363-372.
Zabetakis, Ioannis, "Enhancement of flavour biosynthesis from strawberry (Fragaria x ananassa) callus cultrues by *Methylobacterium* species", Plant Cell, Tissue and Organ Culture (1997) 50: 179-183.
Weerawatanakor, Monthana, et al., "Reactivity and stability of selected flavor compounds", Journal of Food and Drug Analysis (2015) 23: 176-190.
International Search Report from corresponding application PCT/IN2016/050184 dated Oct. 27, 2016.

```
                              SEQUENCE LISTING

<160> NUMBER OF SEQ ID NOS: 13

<210> SEQ ID NO 1
<211> LENGTH: 1181
<212> TYPE: DNA
<213> ORGANISM: Mangifera indica
<300> PUBLICATION INFORMATION:
<301> AUTHORS: Chidley,H.G., Oak,P.S., Deshpande,A.B., Pujari,K.H.,
      Giri,A.P. and Gupta,V.S.
<302> TITLE: Molecular Cloning and Characterization of
      O-Methyltransferase from Mango Fruit (Mangifera indica cv.
      Alphonso)
<303> JOURNAL: Molecular Biotechnology
<304> VOLUME: 58
<305> ISSUE: 5
<306> PAGES: 340-350
<307> DATE: 2016-04-20
<308> DATABASE ACCESSION NUMBER: KP993176
<309> DATABASE ENTRY DATE: 2016-04-20
<313> RELEVANT RESIDUES IN SEQ ID NO: (1)..(1181)

<400> SEQUENCE: 1
accggggatc agagagatcg gagagagaaa atgggatcat tagaagttaa gacattgcta      60
gaaggccaag cagaagtatg gcaatacatg tttggctttg cagactccat ggttttgaag     120
tctgctgtgg agcttcgctt agctgacatt atacattcct atggtggccc aatgtcgttg     180
tcccaaatcg cctcaaaaat tgactccgct tcaccaaaca ttccctacct tggtcgcatc     240
atgagaatgc ttgcccgtaa aggagttttt ggggcacatc gtccatcgga aggaggcgac     300
actacctacg ggttgactca catatcaaca tggcttcgac acgactcgga gctcagtctt     360
gctccaatga tactaatgga aaacaatcta tggcaattag caccatggca ttatcttagc     420
caatgtgtca acaaggtgg aattgctttc aagaaggcgc acgggtgtga gatgtgggac     480
ttcgcatcac aaaaccccga attcaacaag ctgttcaatg atgcccttgc atgcacgacc     540
aagattgtga tgagggcatt tttatcacaa tacaaagagg ggtttaacaa tgtcagatca     600
ctggttgatg tgggtggtgg caccggaggc gagctggccg agattttgaa aacctatcca     660
cacatgaaag gcataaattt tgatctgcca catgttgtag ctactgctcc tgaatatgat     720
ggggtctcaa acgttggagg taacatgttt gatgccattc ctaatgcaga cgtcattttc     780
atgaagtgga tactgcatga ttggagtgat gaagcttgtg tgaagattct gaaaaattgt     840
aggaaagcaa taccggagaa aactgggagg gttgttctag ttgaaatcgt tctgcaggaa     900
aatggtgaca acatgtttgg gaacatggac gtagtgtttg atctactgat gtttgcacac     960
actacagggg gaaaggaaag gactgaacca gaatggaaaa aattattgga ggaaggaggc    1020
tttcctcgct acaatatcat caacatccca gctttaccat ccattattga ggcctatcca    1080
ctgtaacgtc attaatatat tgttgttgcc tgtcatgtca tctgcttgcg agcagggccg    1140
tggaagttct caaatgaatt aataaataca tttcaaaaga t                        1181

<210> SEQ ID NO 2
<211> LENGTH: 1056
<212> TYPE: DNA
<213> ORGANISM: Artificial Sequence
<220> FEATURE:
<223> OTHER INFORMATION: cDNA sequence
<220> FEATURE:
<221> NAME/KEY: misc_feature
<222> LOCATION: (1)..(1050)
<223> OTHER INFORMATION: cDNA
```

```
<400> SEQUENCE: 2
atgggatcat tagaagttaa gacattgcta gaaggccaag cagaagtatg gcaatacatg      60
tttggctttg cagactccat ggttttgaag tctgctgtgg agcttcgctt agctgacatt     120
atacattcct atggtggccc aatgtcgttg tcccaaatcg cctcaaaaat tgactccgct     180
tcaccaaaca ttccctacct tggtcgcatc atgagaatgc ttgcccgtaa aggagttttt     240
ggggcacatc gtccatcgga aggaggcgac actacctacg ggttgactca catatcaaca     300
tggcttcgac acgactcgga gctcagtctt gctccaatga tactaatgga aaacaatcta     360
tggcaattag caccatggca ttatcttagc caatgtgtca acaaggtgg  aattgctttc     420 aagaaggcgc acgggtgtga gatgtgggac ttcgcatcac aaaaccccga attcaacaag     480
ctgttcaatg atgcccttgc atgcacgacc aagattgtga tgagggcatt tttatcacaa     540
tacaaagagg ggtttaacaa tgtcagatca ctggttgatg tgggtggtgg caccggaggc     600
gagctggccg agattttgaa aacctatcca cacatgaaag gcataaattt tgatctgcca     660
catgttgtag ctactgctcc tgaatatgat ggggtctcaa cgttggagg  taacatgtttt     720 gatgccattc ctaatgcaga cgtcattttc atgaagtgga tactgcatga ttggagtgat     780
gaagcttgtg tgaagattct gaaaaattgt aggaaagcaa taccggagaa actgggagg     840 gttgttctag ttgaaatcgt tctgcaggaa aatggtgaca acatgtttgg gaacatggac     900
gtagtgtttg atctactgat gttttgcacac actacagggg gaaaggaaag gactgaacca     960
gaatggaaaa aattattgga ggaaggaggc tttcctcgct acaatatcat caacatccca    1020
gctttaccat ccattattga ggcctatcca ctgtaa                               1056

<210> SEQ ID NO 3
<211> LENGTH: 351
<212> TYPE: PRT
<213> ORGANISM: Artificial Sequence
<220> FEATURE:
<223> OTHER INFORMATION: O-methyltransferase enzyme protein sequence
<220> FEATURE:
<221> NAME/KEY: PEPTIDE
<222> LOCATION: (1)..(351)
<223> OTHER INFORMATION: O-methyltransferase peptide or enzyme sequence

<400> SEQUENCE: 3

Met Gly Ser Leu Glu Val Lys Thr Leu Leu Glu Gly Gln Ala Glu Val
1               5                   10                  15

Trp Gln Tyr Met Phe Gly Phe Ala Asp Ser Met Val Leu Lys Ser Ala
                20                  25                  30

Val Glu Leu Arg Leu Ala Asp Ile His Ser Tyr Gly Gly Pro Met
            35                  40                  45

Ser Leu Ser Gln Ile Ala Ser Lys Ile Asp Ser Ala Ser Pro Asn Ile
        50                  55                  60

Pro Tyr Leu Gly Arg Ile Met Arg Met Leu Ala Arg Lys Gly Val Phe
65                  70                  75                  80

Gly Ala His Arg Pro Ser Glu Gly Gly Asp Thr Thr Tyr Gly Leu Thr
                85                  90                  95

His Ile Ser Thr Trp Leu Arg His Asp Ser Glu Leu Ser Leu Ala Pro
            100                 105                 110

Met Ile Leu Met Glu Asn Asn Leu Trp Gln Leu Ala Pro Trp His Tyr
        115                 120                 125

Leu Ser Gln Cys Val Lys Gln Gly Gly Ile Ala Phe Lys Lys Ala His
    130                 135                 140
```

-continued

Gly Cys Glu Met Trp Asp Phe Ala Ser Gln Asn Pro Glu Phe Asn Lys
145                 150                 155                 160

Leu Phe Asn Asp Ala Leu Ala Cys Thr Thr Lys Ile Val Met Arg Ala
            165                 170                 175

Phe Leu Ser Gln Tyr Lys Glu Gly Phe Asn Asn Val Arg Ser Leu Val
            180                 185                 190

Asp Val Gly Gly Gly Thr Gly Gly Glu Leu Ala Glu Ile Leu Lys Thr
            195                 200                 205

Tyr Pro His Met Lys Gly Ile Asn Phe Asp Leu Pro His Val Val Ala
            210                 215                 220

Thr Ala Pro Glu Tyr Asp Gly Val Ser Asn Val Gly Gly Asn Met Phe
225                 230                 235                 240

Asp Ala Ile Pro Asn Ala Asp Val Ile Phe Met Lys Trp Ile Leu His
            245                 250                 255

Asp Trp Ser Asp Glu Ala Cys Val Lys Ile Leu Lys Asn Cys Arg Lys
            260                 265                 270

Ala Ile Pro Glu Lys Thr Gly Arg Val Val Leu Val Glu Ile Val Leu
            275                 280                 285

Gln Glu Asn Gly Asp Asn Met Phe Gly Asn Met Asp Val Val Phe Asp
290                 295                 300

Leu Leu Met Phe Ala His Thr Thr Gly Gly Lys Glu Arg Thr Glu Pro
305                 310                 315                 320

Glu Trp Lys Lys Leu Leu Glu Glu Gly Gly Phe Pro Arg Tyr Asn Ile
            325                 330                 335

Ile Asn Ile Pro Ala Leu Pro Ser Ile Ile Glu Ala Tyr Pro Leu
            340                 345                 350

<210> SEQ ID NO 4
<211> LENGTH: 26
<212> TYPE: DNA
<213> ORGANISM: Artificial Sequence
<220> FEATURE:
<223> OTHER INFORMATION: MTsI forward primer for partial cDNA sequence
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (18)..(18)
<223> OTHER INFORMATION: Inosine
<220> FEATURE:
<221> NAME/KEY: modified_base
<222> LOCATION: (24)..(24)
<223> OTHER INFORMATION: Inosine

<400> SEQUENCE: 4
gthgacgthg ghgghgghac hgghgc                                  26

<210> SEQ ID NO 5
<211> LENGTH: 23
<212> TYPE: DNA

<213> ORGANISM: Artificial Sequence
<220> FEATURE:
<223> OTHER INFORMATION: MTasIV Reverse Primer for partial cDNA
      synthesis
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (14)..(14)
<223> OTHER INFORMATION: Inosine

<400> SEQUENCE: 5
cagtghtcgt chchccagtc gtg                                           23

<210> SEQ ID NO 6
<211> LENGTH: 25
<212> TYPE: DNA
<213> ORGANISM: Artificial Sequence
<220> FEATURE:
<223> OTHER INFORMATION: Foward Primer for rapid amplification of cDNA
      ends (RACE) to acquire the complete ORF

<400> SEQUENCE: 6
gatctgccac atgttgtagc tactg                                         25

<210> SEQ ID NO 7
<211> LENGTH: 28
<212> TYPE: DNA
<213> ORGANISM: Artificial Sequence
<220> FEATURE:
<223> OTHER INFORMATION: Reverse Primer for rapid amplification of cDNA
      ends (RACE) to acquire the complete ORF

<400> SEQUENCE: 7
aatggcatca aacatgttac ctccaacg                                      28

<210> SEQ ID NO 8
<211> LENGTH: 27
<212> TYPE: DNA
<213> ORGANISM: Artificial Sequence
<220> FEATURE:
<223> OTHER INFORMATION: Forward Primer corresponding to the terminal
      regions of cDNA

<400> SEQUENCE: 8
atgggatcat tagaagttaa gacattg                                       27

<210> SEQ ID NO 9
<211> LENGTH: 25
<212> TYPE: DNA
<213> ORGANISM: Artificial Sequence
<220> FEATURE:
<223> OTHER INFORMATION: Reverse Primer corresponding to the terminal
      regions of cDNA

<400> SEQUENCE: 9
ttacagtgga taggcctcaa taatg                                         25

<210> SEQ ID NO 10
<211> LENGTH: 39
<212> TYPE: DNA
<213> ORGANISM: Artificial Sequence
<220> FEATURE:

```
<223> OTHER INFORMATION: Foward Primer having flanking BamHI site for
      cloning in pGEX-4T expression vector

<400> SEQUENCE: 10
aaaaaaggat ccatgggatc attagaagtt aagacattg                              39

<210> SEQ ID NO 11
<211> LENGTH: 36
<212> TYPE: DNA
<213> ORGANISM: Artificial Sequence
<220> FEATURE:
<223> OTHER INFORMATION: Reverse Primer having flanking BamHI site for
      cloning in pGEX-4T expression vector

<400> SEQUENCE: 11
aaaaaggatc cttacagtgg ataggcctca ataatg                                 36

<210> SEQ ID NO 12
<211> LENGTH: 23
<212> TYPE: DNA
<213> ORGANISM: Artificial Sequence
<220> FEATURE:
<223> OTHER INFORMATION: Forward Primer for amplifying transcripts of
      MiOMTS for semi-quantitative and quantitative PCR

<400> SEQUENCE: 12
atgaagtgga tactgcatga ttg                                               23

<210> SEQ ID NO 13
<211> LENGTH: 24
<212> TYPE: DNA
<213> ORGANISM: Artificial Sequence
<220> FEATURE:
<223> OTHER INFORMATION: Reverse Primer for amplifying transcripts of
      MiOMTS for semi-quantitative and quantitative PCR

<400> SEQUENCE: 13
agaacgattt caactagaac aacc                                              24
```

MOLECULAR CLONING AND EXPRESSION OF CDNA ENCODING O-METHYLTRANSFERASE ISOLATED FROM *MANGIFERA INDICA*

RELATED APPLICATIONS

The present application is a 371 National Stage of PCT/IN2016/050184 filed on 16 Jun. 2016, which claims the benefit of Indian Provisional Patent Application No. 1795/DEL/2015 filed on 16 Jun. 2015.

FIELD OF THE INVENTION

The present invention relates to the cloning and expression of cDNA encoding O-methyl transferase for catalyzing the synthesis of vital volatile flavor compounds such as mesifuran and vanillin, thereby playing a significant role in flavor biochemistry of mango.

The present invention also provide a process for the preparation of volatile compounds by mesifuran, ferulic acid, guaiacol and vanillin, specifically mesifuran and vanillin using cDNA sequence.

BACKGROUND

Mango (*Mangifera indica* L.) is one of the most popular and widely cultivated tropical fruit, mainly due to its attractive flavour. Based on findings (Mukherjee, 1997 and Bompard and Schnell, 1997), the center of origin and diversity of the genus *Mangifera* is now firmly established in Southeast Asia. Several mango cultivars are grown throughout the world and are known to differ evidently in their flavour characteristics. These attributes have resulted in an increased significance of the commercial value of mango.

Volatiles form an indispensable component of flavour in mangoes therefore extensive labor and effort has been invested to decipher this volatile composition of various mango cultivars (Pino and Mesa 2006; Macleod and Pieris 1984; Pandit et al 2009a). Subsequently, all these efforts have put forth together a vast diversity of volatile compounds portrayed by mango cultivars. More than 300 volatile compounds have been identified as free forms and approximately 70 compounds as glycosidically bound compounds. This variability in volatile compounds has been established to depend on the cultivar, maturity stage of the fruit, part of the fruit and processing (Pino et al, 2005).

Amongst the diverse set of cultivars, Alphonso is a highly valued Indian mango cultivar and is grown mainly in the western part of India including Sindhudurg, Ratnagiri and Raigad districts and in the Konkan region of India. Its volatile composition relating to various stages of development and ripening have been analyzed by various researchers (Pandit et al 2009). Although studies revealed that the volatile profile of Alphonso mangoes is dominated by terpene hydrocarbons throughout fruit development and ripening, their impact on the overall flavour of ripe Alphonso was found to be relatively less owing to their high odour detection threshold. Further, to support the theory of minimal impact of terpene hydrocarbons on the flavour profile of Alphonso, studies by Pandit et al. (2009b), and Kulkarni et al (2012) have indicated that similar pattern of terpenes is also detected in flowers and leaves of Alphonso mango and it is the lactones and furanones which are particularly synthesized during the late ripening stages that have significantly low odour detection threshold and thus contribute majority of flavour imparting sweet fruity caramel like notes to ripe Alphonso fruits.

Furanones are widely distributed in nature and have a very low odour threshold value in water i.e. $4 \times 10^{-5}$ mg/kg; hence its effect on food aroma is considerable (Latrasse, 1991). In Alphonso mango, furanones comprise 4-hydroxy-2,5-dimethyl-3(2H)-furanone (furaneol) and its methyl ether, 2,5-dimethyl-4-methoxy-3(2H)-furanone (mesifuran). The importance of these compounds to the flavour of Alphonso mangoes was first evaluated organoleptically by Wilson III et al (1996). Both these compounds have an odour detection threshold of 10 and 0.03 ppb, respectively and thus have high 'aroma value'. Alphonso mangoes showed quantitative dominance of these compounds when compared with other cultivars (Pandit et al. 2009a).

Further, M. Sakho et al (1997) disclose carbohydrate and aglycon moieties released, respectively, by acid and enzymatic hydrolysis of African mango pulp extracts containing glycosidically bound compounds of which vanillin was identified to be one of the components. Vanillin is an industrially produced aroma compound which is a crystalline powder in its isolated form. Due to high consumer perception, naturally prepared vanillin is considered a more suitable food additive and hence it has higher market value as compared to its synthetic version (Priefert et al. 2001). For improved vanillin production by ferulic acid bio-conversion, genetically engineered strain cloned with genes from *P. fluorescens* has been developed by Barghini et al, which was capable of producing vanillin without accumulation of undesirable metabolites. Product inhibition is one of the several problems that the vanillin production encounters (Biotransformation of Waste Biomass into High Value Biochemicals, Satinder, Kaur et al).

Considering the lack of production methods for the synthesis of vanillin and furanones, importance is given to these volatile compounds due to their use in the food and fragrance industry, as chemical intermediates in the production of pharmaceuticals and other fine chemicals. High importance of furanones for the food industry has promoted standardization of their chemical synthesis by various researchers, however; the identification of a suitable biosynthetic process for the production of furaneol and mesifuran is a field still in infancy (Schwab 2013).

Research studies available in the art do not provide for synthesis of vanillin and mesifuran therefore limiting the use of O-methyltransferase. Levid et al (2002) partially purified and biochemically characterized S-adenosyl-L-methionine (SAM) dependent O-methyltransferase from *Fragaria ananassa* i.e. strawberry fruit extracts which displayed active conversion of furaneol to mesifuran in an assay reaction. This was later supported by the molecular isolation of corresponding cDNA followed by the expression of its recombinant protein (FaOMT) which demonstrated successful synthesis of mesifuran from furaneol in an in vitro assay reaction (Wein et al 2002).

Kulkarni et al (2013) have characterized an enone oxidoreductase (MiE0) which catalysed the synthesis of furaneol, a precursor molecule of mesifuran from Alphonso mango to study biosynthesis of furanones in mangoes. Further, ethylene treatment resulted in early and exceptionally enhanced synthesis of mesifuran in Alphonso mango (Chidley et al 2013).

However, in spite of the synthesis of vanillin and mesifuran using biotechnological applications, there is still a need in the art to synthesize these flavour imparting components in higher yield. Therefore the present inventors have isolated and expressed cDNA encoding O-methyltransferase (O-MTS) which catalyze the synthesis of mesifuran from furaneol and vanillin from protocatechuic aldehyde in an in vitro assay reaction.

DETAILED DESCRIPTION OF THE INVENTION

Figure 1:
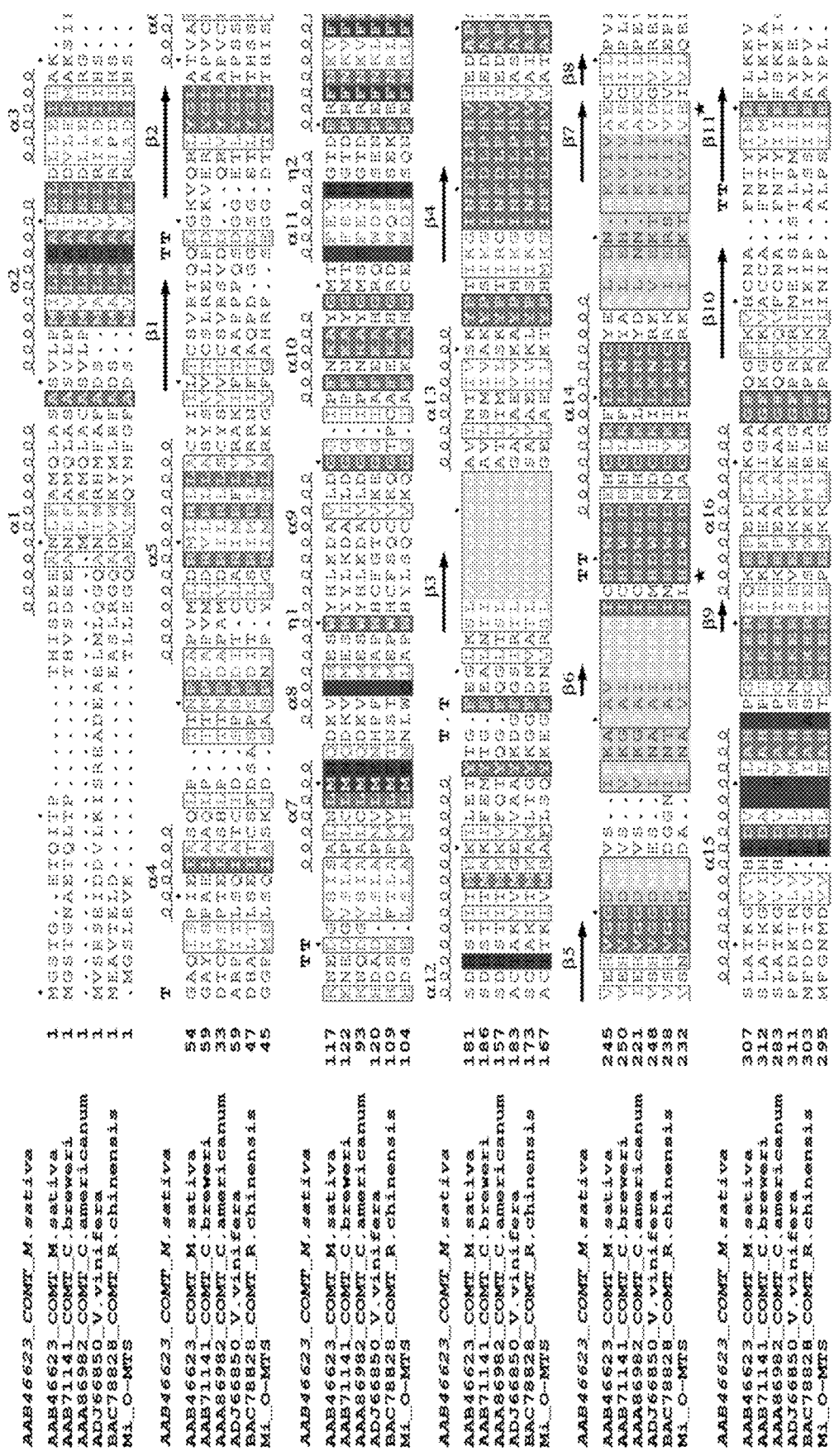
FIG. 1: This figure depicts sequence alignment of in silico translated MiOMTS of the instant invention with O-MTS sequences identified from other plants and disclosed in the art. The active site dimer residues are highlighted in maroon, the substrate binding sites are highlighted in blue, the conserved SAM-binding motifs are highlighted in green and the catalytic residues are indicated by the star below the alignment. The predicted secondary structures are indicated on the top of the alignment.

While the invention is susceptible to various modifications and/or alternative processes and/or compositions, specific embodiment thereof has been shown by way of example in the drawings and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The graphs, tables, figures and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

Definitions

As used herein, the terms "cDNA or nucleotide cDNA or nucleotide or cDNA sequence" when used in the context of the present invention refers to complementary DNA (cDNA) or double-stranded DNA of O-methyltransferase of *Mangifera indica* (MiOMTS) synthesized from a single stranded RNA (e.g., messenger RNA (mRNA) template in a PCR reaction catalysed by the enzyme reverse transcriptase. The cDNA or nucleotide cDNA or nucleotide when used in context of present invention consist of SEQ ID No.2 and encodes for O-methyltransferase protein or enzyme of *Mangifera indica* (MiOMTS). The cDNA or nucleotide cDNA or nucleotide when used in context of present invention consist of SEQ ID No.2 and encodes for O-methyltransferase protein or enzyme of *Mangifera indica* (MiOMTS) having SEQ ID No.3. As used herein, the terms "cDNA or nucleotide cDNA or nucleotide or cDNA sequence" as used in the context of the present invention have been used interchangeably and are meant to have the same definition and meaning as herein described.

As used herein, the terms "MiOMTS or MiOMTS protein or MiOMTS enzyme protein or MiOMTS enzyme or O-methyltransferase" is the O-methyltransferase enzyme protein from *Mangifera indica*, having SEQ ID No.3. As used herein, the terms "MiOMTS or MiOMTS protein or MiOMTS enzyme protein or MiOMTS enzyme or O-methyltransferase" as used in the context of the present invention have been used interchangeably and are meant to have the same definition and meaning as herein described.

The present invention discloses the cloning and expression of cDNA encoding O-methyltransferase of *Mangifera indica* (MiOMTS), which is used in catalyzing the conversion of furaneol to mesifuran and protocatechuic aldehyde to vanillin in industrial scale applications for production of food flavours. More specifically the present invention provides for cloning and expression of cDNA encoding O-methyltransferase of *Mangifera indica* (MiOMTS), which is used in synthesis of volatile compound selected from mesifuran, ferulic acid, guaiacol and vanillin in industrial scale applications for production of food flavours.

In an aspect, the present invention discloses a nucleotide cDNA sequence having SEQ ID No.2 encoding for O-methyltransferase enzyme or protein.

In one aspect, the present invention also provides SEQ ID No. 1 which comprises a complete Open Reading Frame (ORF) encoding O-MTS spanning 1056 bp with 30 bp and 95 bp at the 5' and 3' UTR, respectively (NCBI accession no. KP993176).

In another aspect, the present invention provides a nucleotide or cDNA SEQ ID No. 2 which having at least 90% similarity or is at least 90% identical to SEQ ID No. 1.

The nucleotide sequences of the present invention encode O-methyltransferase of *M. indica*, such that the translated amino acid sequence has a 90% similarity with SEQ ID No.3. The nucleotide sequence of the present invention is to be modified such that the resultant translated amino acid sequence comprises mutations so as to enable the enhancement in the affinity of the enzyme O-MTS and improves it activity.

In an additional aspect, the present invention provides SEQ ID No.2 comprising the coding sequence spanning 1056 bp encoding for protein or amino acid SEQ ID No.3. In another aspect, the present invention provides the expression of cDNA encoding O-methyltransferase in a suitable host cell.

In yet another aspect, the present invention provides recombinantly expressed MiOMTS enzyme showing substrate specificity towards furaneol and protocatechuic aldehyde synthesizing mesifuran and vanillin, respectively.

In one more aspect, the present invention provides a semi-synthetic process for synthesis of volatile compounds by employing O-methyltransferase (O-MTS) comprising;
- (a) expressing recombinant Mi-OMTS comprising Seq ID No.3 encoded by Seq ID No.2 in host cells;
- (b) extracting the said recombinant Mi-OMTS by cell lysis followed by chromatography and filtration to obtain purified protein having molecular weight ranging from 35 to 40 kDa;
- (c) treating the purified protein comprising Seq Id No.3 obtained in step (b) with a suitable substrate and a methyl group donor selected from S-adenosyl methionine (SAM); and
- (d) incubating components of step (c) at 25° C. to 30° C. for 30 min to obtain volatile flavour compounds.

The present invention provides a significant increase in the expression of Mi-OMTS transcripts in ethylene treated mango fruits by cloning and expressing the cDNA sequence having SEQ ID No.2.

In an additional aspect the present invention provides the industrial scale application of the present process employing the present cDNA sequence for the synthesis of flavour compounds such as mesifuran and vanillin.

In an additional aspect the present invention provides the industrial scale application of the present process employing the present cDNA sequence for the synthesis of flavour compounds such as mesifuran and vanillin.

In an additional aspect the present invention provides the industrial scale application of the present process employing the present cDNA sequence for the synthesis of flavour compounds such as mesifuran, ferulic acid, guaiacol and vanillin.

In another aspect the present invention is to increase O-methyltransferase (O-MTS) expression by expressing cDNA encoding O-methyltransferase in higher concentrations.

In another aspect the present invention is to provide a process for increased expression of *Mangifera indica*-OMTS and enhanced production of volatile compounds.

In the present invention mangoes (*Mangifera indica* variety Alphonso mangoes) were collected from Dr. Balasaheb Sawant Konkan Agriculture University, Dapoli, Maharashtra, India.

The fusion expression vector in context of the present invention was obtained from GE Healthcare Life Sciences, Little Chalfont, UK. The fusion expression vector used was pGEX-4T-3 fusion vector.

The host cells used for O-methyltransferase expression were *E. coli* BL21 (DE3) cells which were obtained from Invitrogen, USA. Further *E. coli* host cells (Top10) were obtained from Invitrogen, USA.

The wide range of aroma of several mango cultivars is due to a considerable variation in volatile compounds. Therefore, there is no one typical composition of volatile compounds for this fruit. The present invention is directed to the synthesis of volatile compounds such as mesifuran and vanillin that play an important role in flavour biochemistry of mangoes and other flavoursome fruits by the cloning and molecular expression of the cDNA encoding O-methyltransferase.

The present invention also provides nucleotide SEQ ID No. 1 of O-methyltransferase which was isolated from *Mangifera indica* which comprises the complete Open Reading Frame (ORF) of nucleotide sequence encoding O-MTS spanning 1056 bp containing coding nucleotides and 30 bp and 95 bp 5' and 3' UTR (Untranslated Region), respectively (NCBI accession no. KP993176).

In another aspect of the present invention provides a nucleotide sequence comprising SEQ ID No. 2, wherein the said sequence comprises a nucleotide sequence spanning 1056 bp nucleotides. The said nucleotides sequence selected having SEQ ID No.1 and SEQ ID No.2 encode the polypeptide sequence or protein or amino acid having SEQ ID No.3.

Synthesis of Partial cDNA Fragment:

Ethylene treated fruit pulp having the highest accumulation of mesifuran was selected for the isolation of the partial cDNA sequence encoding O-methyltransferase. A prior art study by Chidley et al. 2013 (Chidley et al., 2013 Food Chemistry 136: 585-594), has indicated that ethylene treated fruit pulp obtained 9 days after harvest (DAH). Therefore, these mangoes were best suited to isolate the partial cDNA sequence, since the mesifuran content is highest in the fruit at this stage.

Accordingly, the partial cDNA sequence of O-methyltransferase (O-MTS) from mango was isolated by employing degenerate primers. Amplification of cDNA from ripened fruits was performed using primers MTsI-MTasIV (Frick and Kutchan 1999 The Plant Journal 17: 329-339). Out of the two pairs of primers used viz. MTsI-MTas II and MTsI-MTasIV, the latter gave the expected size amplicon which was cloned and sequenced to obtain the partial fragment of O-MTS. The primers employed for the synthesis of the partial cDNA sequence amplicon are as follows:

```
MTsI:
                              (SEQ ID No. 4)
5'-GTHGACGTHGGHGGHGGHACHGGHGC-3',

MTasIV:
                              (SEQ ID No. 5)
5'-CAGTGHTCGTCHCHCCAGTCGTG-3',
```

Upon PCR, the amplicons obtained were cloned and sequenced to obtain partial fragments of cDNA encoding O-MTS.

Synthesis of Complete cDNA Sequence

In another aspect the present invention provides synthesis of the complete cDNA sequence of SEQ ID No.1, by rapid amplification of cDNA ends by employing forward primer represented by SEQ ID No.6 and reverse primer represented by SEQ ID No.7 Based on the partial cDNA sequence, gene specific primers were designed for rapid amplification of cDNA ends (RACE) to acquire the complete ORF of O-MTS and are as follows:

```
FP:
                                          (SEQ ID No: 6)
5'-GATCTGCCACATGTTGTAGCTACTG-3',

RP:
                                          (SEQ ID No: 7)
5'-AATGGCATCAAACATGTTACCTCCAACG-3'
(FP: Forward Primer and RP: Reverse Primer)
```

The RACE amplicon sequences obtained were determined for their sequence alignment with O-methyltransferase sequences from other plants disclosed in the NCBI database.

In an embodiment, the complete ORF of Mi-OMTS comprises a 1056 bp long nucleotide sequence with 30 bp and 95 bp 5' and 3' UTR, respectively. The primers corresponding to the terminal regions were designed as follows:

```
FP:
                                          (SEQ ID No: 8)
5'-ATGGGATCATTAGAAGTTAAGACATTG-3',

RP:
                                          (SEQ ID No: 9)
5'-TTACAGTGGATAGGCCTCAATAATG-3'.
```

These primers were used for PCR over ripe Alphonso mango cDNA using Q5 High-Fidelity Taq DNA polymerase (NEB Inc, Ipswich, Mass., USA). The PCR generated amplicons were eluted from agarose gel and ligated to pGEM-T easy vector. The ligation reaction was transformed in *E. coli* cells (Top10) and the recombinant colonies positive for the presence of complete ORF of O-MTS were confirmed by colony PCR followed by sequencing.

Optionally, to decipher the gene structure of O-MTS, the above primers were amplified over Alphonso mango genomic DNA and the obtained fragments were cloned in pGEM-T easy vector and sequenced. The sequences were aligned and the intron-exon junctions were identified by comparing with the cDNA sequence of the O-MTS. The intron-exon junctions are provided in detail in FIG. 2.

Cloning and Recombinant Expression of O-MTS

The complete ORF of O-methyltransferase (Mi-OMTS) was amplified from pGEM-T easy clones using primers having flanking BamHI site for ligation into a fusion vector pGEX-4T-3. The primers used were as follows:

```
FP:
                                          (SEQ ID No: 10)
5'-AAAAAAGGATCCATGGGATCATTAGAAGTTAAGACATTG-3',
and RP:
                                          (SEQ ID No: 11)
5'-AAAAAGGATCCTTACAGTGGATAGGCCTCAATAATG-3'
```

The ligation reaction was transformed into *E. coli* cells (Top10, Invitrogen, USA) and the positive transformants were selected by colony PCR and the orientation of the insert was confirmed by sequencing. The pGEX-4T-Mi-OMTS construct thus obtained was transformed in *E. coli* BL21 (DE3) cells for expression of recombinant O-MTS.

In another aspect the present invention provide the cDNA was isolated from ethylene treated *Mangifera indica* fruit pulp and/or skin.

In another embodiment, the present invention provides MiOMTS protein having Seq Id No.3, wherein the said protein comprises 351 amino acids and has a molecular mass of about 39 Kda and pI of 5.71.

The instant synthesized amino acid sequence of recombinant MiOMTS exhibits 41% identity to the strawberry O-methyltransferase (FaOMTS) which is the only characterized O-methyltransferase involved in the biosynthesis of mesifuran, and 74% identity to *Ricinus communis* and *Populus trichocarpa* O-methyltransferases which are not yet characterized for their enzymatic activity.

Moreover, the amino acid alignment of MiOMTS with other plant O-MTS s showed the presence of conserved motifs essential for the SAM and substrate binding as shown in the sequence alignment indicated in FIG. 1.

The alignment of in silico translated amino acid sequence of MiOMTS with other representative plant O-methyltransferases showed the presence of highly conserved motifs for substrate and SAM (S-adenosyl-L-methionine) binding along with important catalytic residues.

In another embodiment, the complete ORF of MiOMTS cDNA cloned in pGEX-4T vector was expressed as GST-tag fusion protein in *E. coli* BL21 (DE3) cells followed by protein purification.

Figure 3:
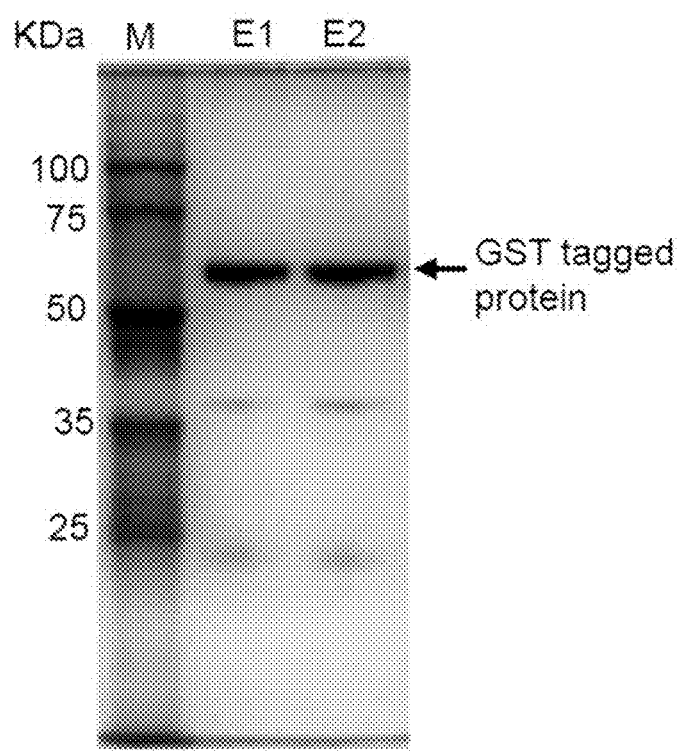
FIG. 3: This figure depicts SDS-PAGE profile of GST-bound MiOMTS protein, E1 and E2 refers to elution fractions and M is the marker protein.

The expressed protein was purified using GST affinity chromatography and released from the tag using thrombin. The fusion protein showed the size of ~66 kDa confirming the expression of recombinant MiOMTS. SDS-PAGE profile of GST-bound MiOMTS protein is shown in FIG. 3.

In another aspect the present invention provides increased specificity of the instant recombinant O-methyltransferase to furaneol and protocatechuic aldehyde, thereby providing improved yield of mesifuran and vanillin, respectively.

Figure 5:
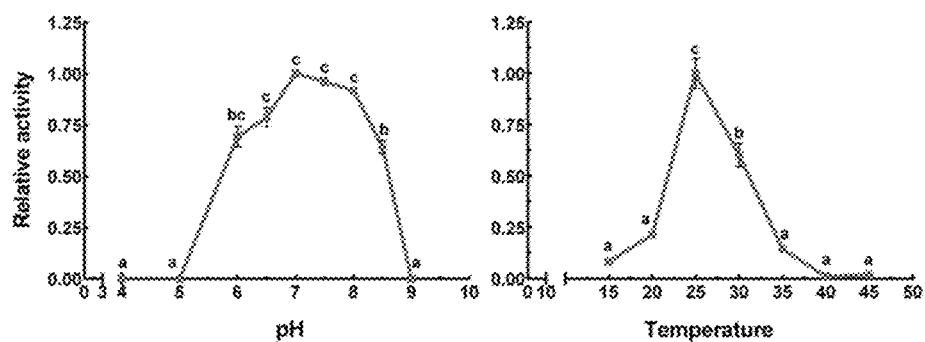
FIG. 5: This figure depicts optimum conditions of pH and temperature for the activity of MiOMTS. In case of both the parameters, the peak area of the product at the highest activity was considered as 1and relative activity was calculated for rest of reactions. Letters at each point indicate the significance of ANOVA (p≤0.05) analyzed by Fisher's LSD test independently for both the parameters; the values with different letters are significantly different from each other.

The optimum activity for the recombinant MiOMTS was recorded at pH 7.0 and 25° C. temperature as depicted in FIG. 5.

In one more aspect the present invention provides a semi-synthetic process for synthesis of volatile compounds by employing O-methyltransferase (O-MTS) comprising
  (a) expressing recombinant Mi-OMTS comprising Seq Id No.3 encoded by Seq Id No.1 in host cells;
  (b) extracting the said recombinant Mi-OMTS by cell lysis followed by chromatography and filtration to obtain purified protein having molecular weight ranging from 35 kDa to 40 kDa;
  (c) treating the purified protein comprising Seq Id No.3 obtained in step (b) with a suitable substrate and a methyl group donor selected from S-adenosyl methionine (SAM); and
  (d) incubating components of step (c) at 25° C. to 30° C. for 30 min to obtain volatile flavour compounds.

Accordingly, the process for volatile compound preparation comprises expressing the presently synthesized cDNA sequence in host cells, *E. coli* BL21 cells are suitably used as host cells to obtain the intracellular expression of the O-methyltransferase. Post expression of the recombinant enzyme cells are subjected to lysis for release of the intracellular components as the lysate. The lysate comprising the recombinant protein additionally has the presence of other compounds and other extraneous matter that may be eliminated by affinity chromatography followed by filtration processes. The purified protein obtained has a molecular weight of about 35 to 40 kDa, having optimum pH of 7 and optimum activity at 25° C.

The purified protein is treated with a suitable substrate which may be selected from furaneol, caffeic acid, catechol and protocatechuic aldehyde in the presence of a methyl donor, namely S-adenosyl methionine (SAM) to obtain the volatile compounds mesifuran, ferulic acid, guaiacol and vanillin respectively.

Advantageously, the present invention provides recombinant O-methyltransferase enzyme with the highest activity at pH 7.0 and temperature 25° C. and high substrate specificity towards furaneol and protocatechuic aldehyde, thereby resulting in the increased synthesis of industrially important end products such as mesifuran and vanillin respectively. As mesifuran and vanillin carry industrial importance from flavour and fragrance point of view, MiOMTS has potential biotechnological application in the flavour production industries which can be delved into.

Accordingly, the main embodiment of the present invention provides a nucleotide SEQ ID No.2 encoding for *Mangifera indica* O-methyltransferase (Mi-OMTS) protein.

Accordingly, the main embodiment of the present invention provides a nucleotide SEQ ID No.2 encoding for *Mangifera indica* O-methyltransferase (Mi-OMTS) enzyme protein.

Another embodiment of the present invention provides a nucleotide ID No. 2 which encodes for *Mangifera indica* O-methyltransferase (Mi-OMTS) protein is having SEQ ID No.3.

Another embodiment of the present invention provides a nucleotide ID No. 2 which encodes for *Mangifera indica* O-methyltransferase (Mi-OMTS) enzyme protein is having SEQ ID No.3.

Yet another embodiment of the present invention provides a protein molecule having SEQ ID No.3 encoding for *Mangifera indica* O-methyltransferase (Mi-OMTS).

Yet another embodiment of the present invention provides a protein molecule having SEQ ID No.3 encoding for *Mangifera indica* O-methyltransferase (Mi-OMTS) obtained from nucleotide SEQ ID No.2.

One more embodiment of the present invention provides a recombinant expression vector comprising nucleotide SEQ ID No. 2.

One more embodiment of the present invention provides a recombinant expression vector comprising nucleotide SEQ ID No. 2 encoding for *Mangifera indica* O-methyltransferase (Mi-OMTS) protein having SEQ ID No.3.

One more embodiment of the present invention provides a recombinant expression vector comprising nucleotide SEQ ID No. 2 encoding for *Mangifera indica* O-methyltransferase (Mi-OMTS) enzyme protein having SEQ ID No.3.

Another embodiment of the present invention provides recombinant expression vector as herein described wherein the said recombinant expression vector is selected from pGEX-4T, pGEX-2T, pGEX-3X, pGEX-5X and pGEX-6P.

Another embodiment of the present invention provides a recombinant expression vector as herein described wherein the said recombinant expression vector is pGEX-4 T.

Yet another embodiment of the present invention provides a host cell comprising the recombinant expression vector as herein described wherein the said host cell is *Escherichia coli*.

Another embodiment of the present invention provides a host cell comprising the DNA molecule of SEQ ID No. 2, wherein the said host cell is *Escherichia coli*.

Another embodiment of the present invention provides a process for synthesis of volatile compounds said process comprising the steps of:
  (a) cloning Mi-OMTS nucleotide SEQ ID No. 2 in a recombinant expression vector;
  (b) inserting the recombinant expression vector of step (a) in *E. coli*;
  (c) expressing Mi-OMTS nucleotide SEQ ID No. 2 to produce Mi-OMTS protein having SEQ ID No. 3 in *E. coli*;
  (d) extracting the said Mi-OMTS protein of step (c) by *E. coli* cell lysis;
  (e) carrying out chromatography and filtration of the extracted protein of step (d) to obtain purified protein having molecular weight ranging from 35 kDa to 40 kDa;
  (f) treating the purified protein of step (e) with a suitable substrate and a methyl group donor selected from S-adenosyl methionine (SAM); and
  (g) incubating components of step (f) at a temperature of 25° C.–30° C. for 30 min to obtain volatile flavour compounds.

Another embodiment of the present invention provides a process as herein described wherein the substrate in step (e) of the process is selected from furaneol, caffeic acid, catechol and protocatechuic aldehyde.

Another embodiment of the present invention provides a process as herein described wherein the volatile compounds are selected from mesifuran, ferulic acid, guaiacol and vanillin.

Another embodiment of the present invention provides a process as herein described wherein the volatile compounds are mesifuran and vanillin.

Yet another embodiment of the present invention provides use of SEQ ID No. 2 for synthesizing volatile compounds selected from mesifuran, ferulic acid, guaiacol and vanillin.

Yet another embodiment of the present invention provides use of SEQ ID No. 2 for synthesizing volatile compounds mesifuran and vanillin.

Yet another embodiment of the present invention provides use of SEQ ID No. 3 for synthesizing volatile compounds selected from mesifuran, ferulic acid, guaiacol and vanillin.

Yet another embodiment of the present invention provides use of SEQ ID No. 3 for synthesizing volatile compounds mesifuran and vanillin.

In one embodiment the present invention provides use of SEQ ID No. 2 in a method for synthesizing volatile compounds selected from mesifuran, ferulic acid, guaiacol and vanillin.

In one embodiment the present invention provides use of SEQ ID No. 2 in a method for synthesizing volatile compounds mesifuran and vanillin.

In one embodiment the present invention provides use of SEQ ID No. 3 in a method for synthesis volatile compounds selected from mesifuran, ferulic acid, guaiacol and vanillin.

In one embodiment the present invention provides use of SEQ ID No. 3 in a method for synthesis volatile compounds mesifuran and vanillin.

One embodiment of the present invention a method of synthesizing volatile compounds selected from mesifuran, ferulic acid, guaiacol and vanillin using SEQ ID No. 2. One embodiment of the present invention provides a method of synthesizing volatile compounds mesifuran and vanillin using SEQ ID No. 2.

One embodiment of the present invention provides a method of synthesizing volatile compounds selected from mesifuran, ferulic acid, guaiacol and vanillin using SEQ ID No. 3.

One embodiment of the present invention provides a method of synthesizing volatile compounds mesifuran and vanillin using SEQ ID No. 3.

Another embodiment of the present invention provides a process for synthesis of volatile compounds said process comprising the steps of:
  (a) expressing Mi-OMTS protein having SEQ ID No. 3 in *E. coli;*
  (d) extracting the said Mi-OMTS protein of step (c) by *E. coli* cell lysis;
  (e) carrying out chromatography and filtration of the extracted protein of step (d) to obtain purified protein having molecular weight ranging from 35 kDa to 40 kDa;
  (f) treating the purified protein of step (e) with a suitable substrate and a methyl group donor selected from S-adenosyl methionine (SAM); and
  (g) incubating components of step (f) at a temperature of 25° C.–30° C. for 30 min to obtain volatile flavour compounds.

The following examples provides a convenient illustration for implementing exemplary embodiments of the invention various changes to the described embodiments may be made in the functions and arrangement of the elements described without departing from the scope of the invention.

Example 1: Effect of Ethylene Treatment on Ripening Stages of Mangoes

Two sets of twenty mature green fruits of Alphonso mango were collected from three distinct mango trees located in the mango orchards of Dr. Balasaheb Sawant Konkan Agriculture University, Dapoli. Harvesting of fruits, subjecting them to ethylene treatment and ripening conditions were performed by processes described in Chidley et al (2013). The harvested fruits were immediately cut, the skin and pulp were separated and frozen in liquid nitrogen, this stage was considered as 'mature raw' which is designated as 0 DAH (days after harvest) stage of control fruits. For ethylene treated fruits, 1 DAH (mature raw) corresponds to 0 DAH of control fruits due to 24 h ethylene treatment given to this set of mangoes after harvest. In accordance with the ripening indices studied by Bandyopadhyay & Gholap, (1973), Alphonso fruit takes a period of 15 days after harvest (15 DAH) for complete ripening by traditional processes, and the 20$^{th}$ day after harvest was denoted as over-ripe stage based on biochemical and molecular analysis of various ripening stages of Alphonso mango performed (Pandit et. al. 2009 a, b).

Thus, the subsequent five ripening stages of control fruits are the following: table green (2DAH), pre-climacteric (5DAH), mid-ripe (10DAH), ripe (15DAH) and over-ripe (20DAH) were frozen to cover the entire ripening period of control fruits.

In case of fruits subjected to ethylene treatment, all six ripening stages occurred within a time interval of 11 days due to accelerated ripening of fruits. Thus, to span the entire period of ripening upon ethylene treatment, the fruits were frozen and stored at table green (3DAH), pre-climacteric (5DAH), mid-ripe (7DAH), ripe (9DAH) and over-ripe (11DAH) stages. In this manner, six ripening stages each for pulp and skin of control and ethylene treated fruits were sampled along with mature leaf and open flowers and stored at −80° C. until further use.

Example 2

(i) RNA Isolation and cDNA Synthesis

Total RNA was isolated from all the tissues under study using RNeasy Plus mini kit (Quiagen, Venlo, Netherlands). Two microgram of total RNA was subjected to reverse transcription using Applied Biosystem High Capacity reverse transcription kit employing oligodT.

(ii) Isolation and Identification of O-Methyltransferase cDNA from *Mangifera indica* Fruits Partial cDNA sequence of O-methyltransferase (O-MTS) from mango was isolated by employing degenerate primers earlier reported by Frick and Kutchan (1999). Amplification was performed using cDNA of 9DAH ethylene treated fruit pulp since prior studies by Chidley et al. 2013, had established the highest accumulation of mesifuran at this stage. Out of the two pairs of primers used viz. MTsI-MTas II and MTsI-MTasIV, the latter gave the expected size amplicon which was cloned and sequenced to obtain the partial fragment of O-MTS. Based on the cDNA sequence, gene specific primers were designed, and are as follows:

```
FP:
                                       (SEQ ID No: 6)
5'-GATCTGCCACATGTTGTAGCTACTG-3',

RP:
                                       (SEQ ID No: 7)
5'-AATGGCATCAAACATGTTACCTCCAACG-3'
(FP: Forward Primer and RP: Reverse Primer)
```

These primers were used for the rapid amplification of cDNA ends (RACE) to acquire the complete open reading frame (ORF) of O-MTS using SMART™ RACE cDNA Amplification Kit (Clontech, USA).

The RACE amplicon sequences thus obtained were aligned with the other plant O-methyltransferase sequences reported in the NCBI database and the primers corresponding to the terminal regions were designed as follows:

```
FP:
                                       (SEQ ID No: 8)
5'-ATGGGATCATTAGAAGTTAAGACATTG-3'
and RP:
                                       (SEQ ID No: 9)
5'-TTACAGTGGATAGGCCTCAATAATG-3'.
```

Figure 2:
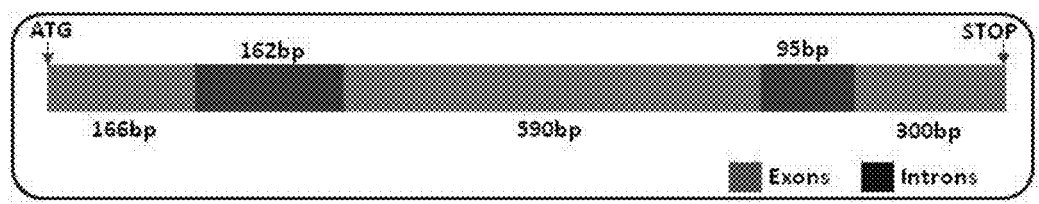
FIG. 2: This figure depicts gene organization of MiOMTS wherein the lengths (bp) of the introns and the exons are indicated, respectively.

The sequence showed high similarity to O-methyltransferase sequences from other plants. The complete ORF of MiOMTS was 1056 bp long with 30 bp and 95 bp 5' and 3' UTR, respectively. The in silico translated MiOMTS protein was 351 amino acids long with the predicted molecular mass of about 39 Kda and pI of 5.71. As per the classification based on the length of plant O-MTSs, proteins in Pl-OMT I group are of 231-248 amino acids long while that of Pl-OMT II group possess 344-383 amino acids (Joshi and Chiang 1998). Thus, MiOMTS can be classified in to Pl-OMT II group. The putative amino acid sequence of MiOMTS showed 41% identity to the strawberry O-methyltransferase (FaOMTS) which is the only characterized O-methyltransferase involved in the biosynthesis of mesifuran. MiOMTS also showed 74% identity to *Ricinus communis* and *Populus trichocarpa* O-methyltransferases which are however not yet characterized for their enzymatic activity. The alignment of in silico translated amino acid sequence of MiOMTS with other representative plant O-methyltransferases showed the presence of highly conserved motifs for substrate and SAM binding along with important catalytic residues. The prediction of secondary structure was performed using the primary (GenBank protein database) and secondary structure of COMT from *M. sativa* (alfalfa; AAB46623) depicting α-helices and β-strands in the structure using ESPript 3.0 software (FIG. 1). The amplicons obtained after the PCR of gene specific terminal primers of O-MTS on genomic DNA template revealed a size of about 1.3 kb and the sequence analysis showed the presence of two introns with 165 bp and 95 bp length. Both the introns followed the "GT-AG" rule (Breathnach and Chambon, 1981) (FIG. 2).

These primers were again used for PCR over ethylene treated ripe stage (9DAH) fruit pulp cDNA using Q5 High Fidelity Taq DNA polymerase (NEB Inc, Ipswich, Mass., USA). The PCR generated amplicons were eluted from agarose gel and ligated to pGEM-T easy vector (Promega, Madison, Wis., USA). The ligation reaction was transformed in *E. coli* cells (Top10) and the recombinant colonies positive for the presence of complete ORF of O-MTS were confirmed by colony PCR followed by sequencing.

Example 3: Cloning and Recombinant Expression of O-MTS

The complete ORF of *Mangifera indica* O-methyltransferase (MiOMTS) was amplified from pGEM-T easy clones using primers having flanking BamHI site for ligation into pGEX-4T-3 fusion vector (GE Healthcare Life Sciences, Little Chalfont, UK). The primers used were as follows:

```
FP:
                            (SEQ ID No: 10)
5'-AAAAAAGGATCCATGGGATCATTAGAAGTTAAGACATTG-3',
and RP:
                            (SEQ ID No: 11)
5'-AAAAAGGATCCTTACAGTGGATAGGCCTCAATAATG-3'.
```

The ligation reaction was transformed into *E. coli* cells (Top10, Invitrogen, USA) and the positive transformants were selected by colony PCR and the orientation of the insert was confirmed by sequencing. The pGEX-4T-MiOMTS construct thus obtained was transformed in *E. coli* BL21 (DE3) cells (Invitrogen, USA) for expression of recombinant O-MTS. The starter culture was grown for 12-13 hr at 37° C. and was used as inoculum in the expression media at the final concentration of 1%.

The expression of recombinant protein was induced by 0.1 mM IPTG when the absorbance, i.e. $OD_{600}$ reached 0.55. Thereafter, the culture was cultivated for 5 hr at 16° C. The cells were harvested by centrifugation and the pellet was suspended in the lysis buffer containing 140 mM NaCl, 2.7 mM KCl, 10 mM $Na_2HPO_4$, 1.8 mM $KH_2PO_4$, 1% glycerol and 2 mMβ-mercaptoethanol (pH 7.3). The clear lysate obtained after sonication and centrifugation was incubated with the pre-equilibrated GST-affinity purification resin (GE Healthcare Life Sciences, Little Chalfont, UK) for 2 hr at 4° C. Unbound proteins were removed by washing the resin 5-7 times with the lysis buffer. Further, the cleavage of the recombinant protein from the GST-tag was carried out using thrombin according to the manufacturer's instructions (GE Healthcare Life Sciences, Little Chalfont, UK), for over-night at 4° C. with gentle agitation. The recombinant protein was collected by fractionation and used for enzyme assays as well as SDS-PAGE.

Figure 4:
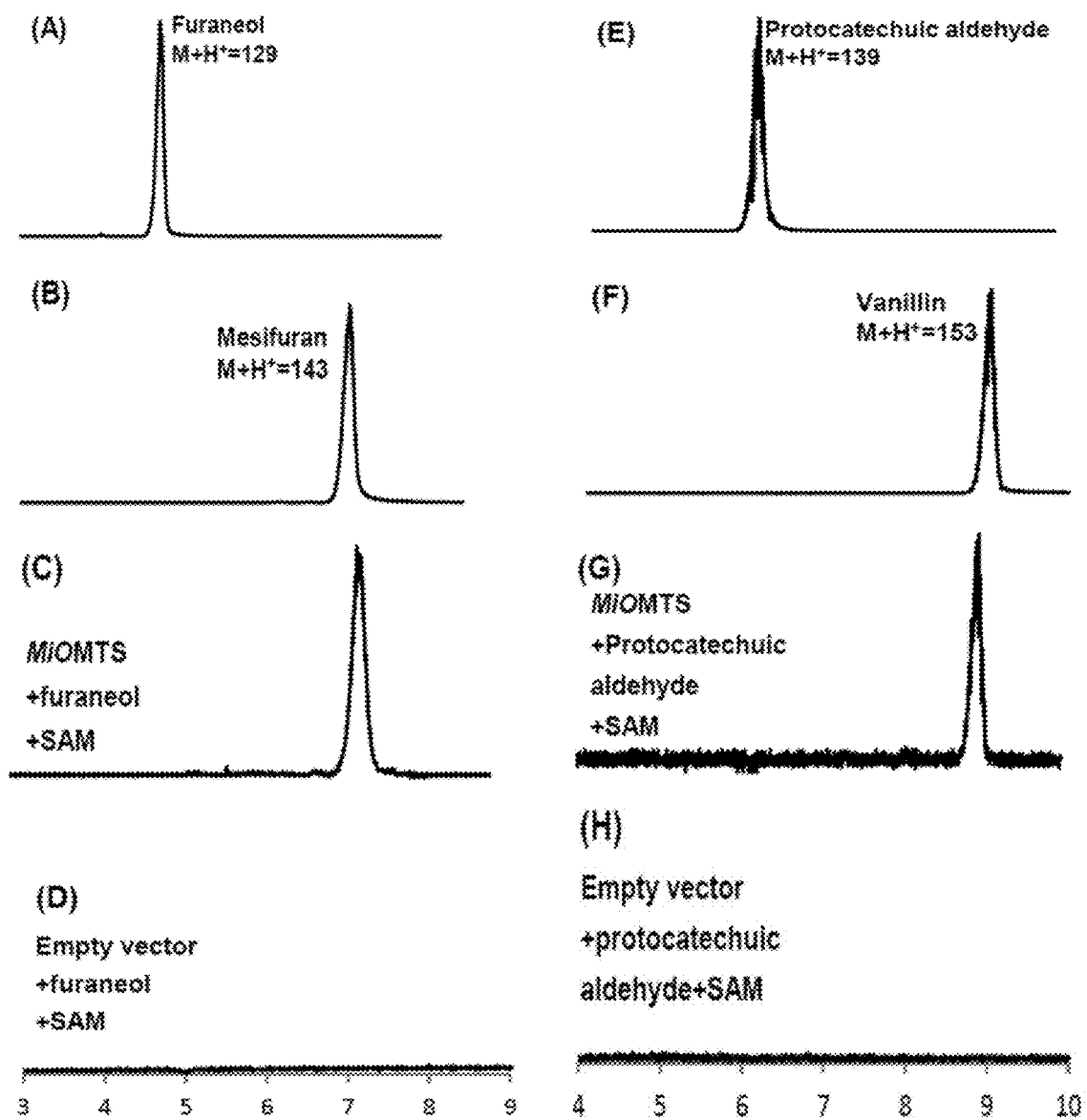
FIG. 4: This figure depicts Extracted Ion chromatograms (EIC) of MiOMTS enzymatic reactions analysed on Q-Exactive-Orbitrap mass spectrometer representing the authentic standards of substrates and their expected products (A, B and E, F), assay products of MiOMTS with furaneol (C) and protocatechuic aldehyde (G) and assay reactions of protein from empty vector with furaneol and protocatechuic aldehyde monitored for (M+H$^+$) ion of their respective product (D and H)

Example 4: Heterologous Expression, Purification and Characterization of Recombinant MiOMTS The complete ORF of MiOMTS cDNA was cloned in pGEX-4T vector and the protein was expressed as GST-tag fusion protein in *E. coli* BL21 (DE3) cells. The protein was purified using GST affinity chromatography and released from the tag using thrombin. The fusion protein showed the size of ~66 kDa confirming the expression of recombinant MiOMTS (FIG. 3). The purified protein was assayed for its activity with furaneol, caffeic acid, catechol and protocatechuic aldehyde as substrates and S-adenosyl-L-metheonine (SAM) as methyl group donor. The methylation products of these substrates upon MiOMTS enzymatic reaction were identified and analysed on high resolution mass spectrometer. The recombinant MiOMTS successfully used for methylation of furaneol and protocatechuic aldehyde as the substrates converting them to mesifuran and vanillin, respectively, in independent reactions. The activity of MiOMTS was confirmed by carrying out the similar assay reaction with the protein of *E. coli* BL21 (DE3) cells transformed with empty pGEX-4T vector which did not show the formation of methylation products in the respective assay reactions (FIG. 4). In contrast to furaneol and protocatechuic aldehyde, MiOMTS could not use caffeic acid and catechol as the methyl group acceptor.

In order to evaluate the optimum biochemical conditions for the activity of recombinant MiOMTS, assays were performed at varied pH and temperatures using furaneol as a substrate. The exercise displayed optimum activity of MiOMTS at pH 7.0 with the retention of 70 and 90% activity at pH 6.0 and 8.0, respectively. However, no activity was detected at pH 4, 5 and 9 with more than 50% reduction in the activity at pH 8.5. In case of temperature, optimum activity was detected at 25° C., with retention of 60% activity at 30° C. However, more than 50% reduction in the activity at 20° C. and complete inactivation of the enzyme at 40° C. was clearly evident (FIG. 5).

Figure 6:
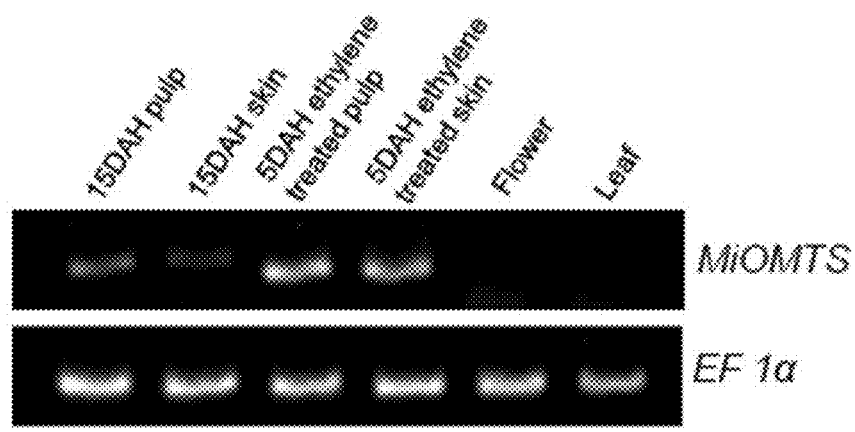
FIG. 6: This figure depicts tissue specific expression of MiOMTS transcripts as evaluated by semi-quantitative PCR. Elongation factor 1α (EF1α) was used as endogenous control.

In conventionally ripened Alphonso mango, mesifuran was detected at 10DAH stage both in pulp and skin separately with subsequent increase in its content till 20DAH. However, in ethylene treated fruits, it was detected although with very minor quantities at 1DAH stage with significantly enhanced synthesis thereafter till 11DAH (Chidley et. al. 2013). The expression pattern of MiOMTS in the pulp and skin of conventionally ripened Alphonso mango showed prominent correlation with the synthesis of mesifuran (FIG. 6). Moreover, in a semi-quantitative PCR analysis, MiOMTS transcripts depicted fruit specific expression while no transcripts were detected in leaf and flowers of Alphonso (FIG. 5).

In case of ethylene treated fruits the transcript accumulation was seen even at 1DAH with steady but significant increase in its expression till 5DAH. After 5DAH, steady decline in the transcript abundance was evident despite a continuous increase in the mesifuran synthesis. This might be due to the substantial synthesis of MiOMTS transcripts and thereby the corresponding protein at preceding stage which continuously catalyzed the production of mesifuran from furaneol in vivo during further ripening stages.

Example 5: Quantitative Real-Time PCR

Quantitative real-time PCR was performed using Fast Start Universal SYBR Green master mix (Roche Inc. Indianapolis, Ind., USA) and elongation factor 1α as an endogenous control employing the primers mentioned earlier (Pandit et al., 2010). Transcripts of MiOMTS were amplified using primers;

```
FP:
                                    (SEQ ID No: 12)
5'-ATGAAGTGGATACTGCATGATTG-3',
and RP:
                                    (SEQ ID No: 13)
5'-AGAACGATTTCAACTAGAACAACC-3'
```

Quantification was done by ViiA™ 7 Real-Time PCR System (Applied Biosystems, CA, USA) having thermal cycle programme of initial denaturation at 95° C. for 10 min with subsequent 40 cycles of 95° C. for 3 sec and 60° C. for 30 sec followed by a dissociation curve analysis of transcripts. Considering the transcript abundance at 5DAH (ethylene treated fruit) as 1, the fold difference in the transcript levels of MiOMTS gene in rest of the tissues was calculated. The quantification was done for three independent biological replicates separately, each of which was represented by at least three technical replicates. A semi-quantitative PCR was performed using above mentioned gene specific primers over 15DAH (control) pulp and skin, 5DAH (ethylene treated) pulp and skin, leaf and flower cDNAs. Twenty micro liter PCR reaction contained 1 µl of the cDNA along with 1× final concentration of Pfu buffer (Promega, Madison, Wis., USA), 2.0 mM $MgCl_2$, 0.5 mM dNTPs, 0.5 µM of each gene specific primer and 1 unit Pfu DNA polymerase (Promega, Madison, Wis., USA). The thermal cycling programme consisted of initial denaturation at 95° C. for 3 min with subsequent 30 cycles of 95° C. for 30 sec, 60° C. for 30 sec followed by extension at 72° C. for 30 sec. The uniformity of expression across the tissues was monitored using elongation factor 1α (EF1α) gene as an endogenous control. Equal amount of loading dye (6λ) with 1λ final concentration of GelRed (Biotium Inc. Hayward, Calif.) was added to the PCR products for visualisation and the PCR products were run through 2% agarose gel.

Example 6

Enzyme Assays and Identification of the Assay Products

The in vitro enzymatic assays were carried out in the lysis buffer containing appropriate amount of protein, 0.2 mM substrate and 0.01 mM S-adenosylmetheonine (SAM) in a final volume of 500 µl reaction. The reaction was incubated at 30° C. for 30 min. For the determination of optimum pH for the enzyme activity, the assays were performed in 50 mM citrate buffer (pH 4.0 and 5.0), 50 mM phosphate buffer (pH 6.0, 6.5, 7.0 and 7.5) and 50 mM Tris buffer (pH 8.0, 8.5 and 9.0) keeping other components in the assay same as above. Similarly, for optimum temperature the assays were performed at 15, 20, 25, 30, 35 and 40° C. Assay products were extracted twice with ethyl acetate; the organic layers were pooled, dried in a concentrator and constituted with methanol. An Accela™ ultra high performance liquid chromatography (UHPLC) system (ThermoFisher, Waltham, USA), coupled online via heated electrospray ionization source (HESI) with a Q-Exactive-Orbitrap mass spectrometer (ThermoFisher), was employed with 20 µL sample injection volume and the chromatograms were obtained by total ion monitoring in a positive ion mode. The products were separated and analysed on Hypercil GOLD C-18 reverse phase column (150 mm×3 mm i. d., particle size 5 µm, Thermo Scientific, Waltham, Mass., USA) with a linear gradient of 95% water acidified with 0.05% formic acid and 5% methanol to 80% methanol and 20% water with the flow rate of 0.5 µl $min^{-1}$. The sample manager was maintained at 4° C. Identification of the substrates as well as products were done by comparing the retention time and molecular mass of authentic external standards [furaneol (CAS No. 3658-77-3), mesifuran (CAS No. 4077-47-8), protocatechuic aldehyde (CAS No. 139-85-5) and vanillin (CAS No. 121-33-5)] procured from Sigma Aldrich, USA.

Example 7

Figure 7:
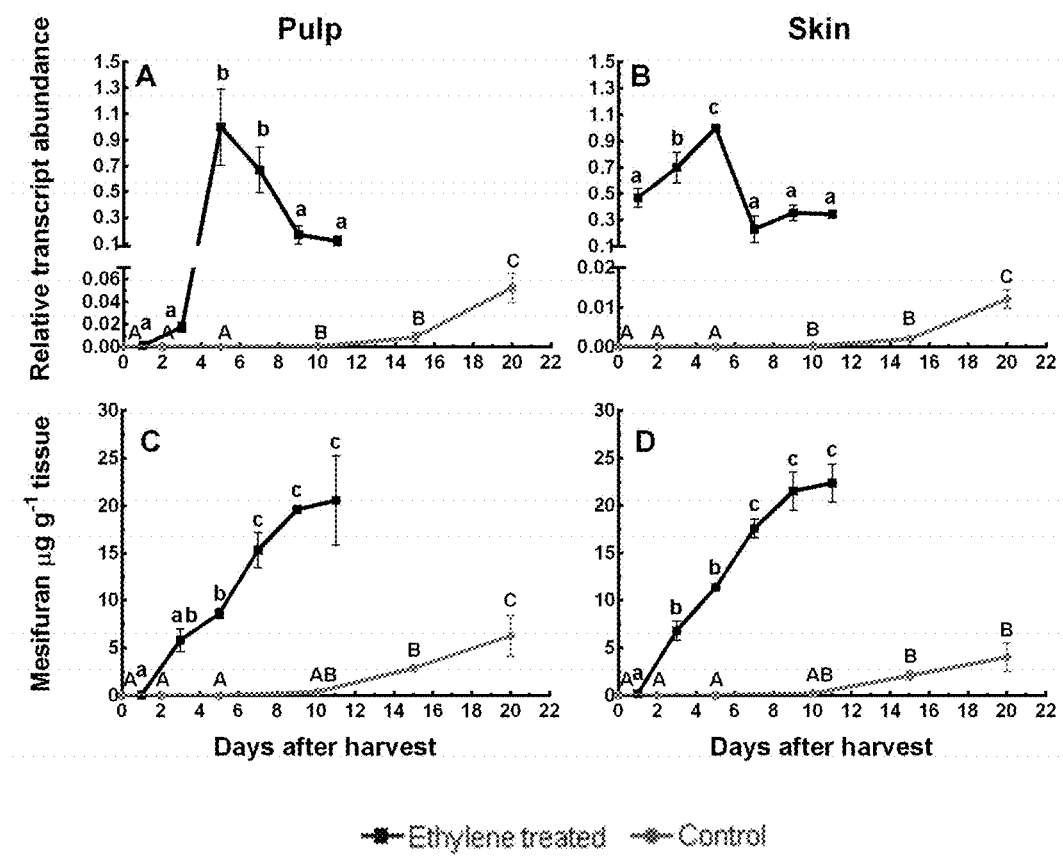
FIG. 7: This figure depicts the relative transcript abundance of MiOMTS transcripts in pulp (A) and skin (B) of control and ethylene treated fruits along with the quantity of mesifuran in pulp (C) and skin (D) of ethylene treated fruits. Vertical bars at each point represent standard error of measurement among the biological replicates and letters at each point indicate the significance of ANOVA (p≤0.05) analysed by Fisher's LSD test.

Correlation of MiOMTS Transcript Abundance and Mesifuran Synthesis During the Ripening of Alphonso Mango and Role of Pre-Climacteric Exogenous Ethylene Treatment To evaluate the tissue specificity of MiOMTS transcripts, a semi-quantitative PCR performed among pulp and skin of control and ethylene treated fruits along with leaf and flower tissues showed expression of MiOMTS only in the pulp and skin of Alphonso fruits suggesting fruit specific expression of the MiOMTS transcripts (FIG. 6). To get better understanding of synthesis of mesifuran during late ripening stages of Alphonso mango and its regulation at transcriptional level, the transcripts of MiOMTS were profiled during the conventional ripening of Alphonso mango. A previous study by the present inventors showed exceptionally high synthesis of mesifuran in the ethylene treated fruits during ripening compared to conventionally ripened fruits (Chidley et al. 2013). To further assess this at transcript level, the transcripts of MiOMTS were analyzed in the fruits which were subjected to the postharvest ethylene treatment. Both pulp and skin of the control and ethylene treated fruits were analyzed separately for the transcript abundance. In case of control fruits, no transcripts were detected in both pulp and skin till 10DAH stage. Thereafter, a steady increase in the transcript level was observed in both the cases till 20DAH. This can be easily correlated to the synthesis of mesifuran during the conventional ripening of Alphonso mango wherein mesifuran was detected at 10, 15 and 20DAH stages only (FIG. 7). However, in the pulp of ethylene treated fruits, the transcript of MiOMTS were detected even at 1 and 3DAH, although at relatively low level. Moreover, a sudden surge in the transcripts was observed at 5DAH stage of pulp as well as skin of ethylene treated fruits which was 19 and 82 fold higher than abundance at 20DAH pulp and skin of conventionally ripened fruits, respectively. Thus, 5DAH stage of ethylene treated fruits remained the highest transcript accumulation stage among the entire data set. Past this stage, a decline in the transcripts was observed both in pulp and skin ripening stages. Such a high expression level of MiOMTS in the ethylene treated fruits clearly explained exceptionally high mesifuran content in the fruits treated by ethylene (FIG. 7).

The correlation analysis performed suggested strong positive correlation between the mesifuran content and MiOMTS transcripts in the pulp ($R^2$=0.95) and skin ($R^2$=0.94) of the control fruits. Although, no such significant correlation was observed in the ripening stages of the ethylene treated fruits (data not shown), it can be noted that ethylene treatment results in strong up-regulation of both mesifuran content and MiOMTS transcript levels (FIG. 7).

Example 8: Statistical Analysis

Comparison of MiOMTS transcripts at various ripening stages of pulp and skin of control and ethylene treated fruits as well as correlations between the mesifuran content and transcript abundance during the ripening stages of pulp and skin of control fruits were carried out by ANOVA using fisher's LSD test at $p \leq 0.05$ using StatView software, version 5.0 (SAS Institute Inc., Cary, N.C., USA).

The invention claimed is:

1. A host cell comprising a recombinant expression vector comprising a cDNA molecule comprising a nucleotide sequence of SEQ ID No.2 encoding an O-methyltransferase protein of *Mangifera indica* (MiOMTS).

2. The host cell according to claim 1, wherein the nucleotide sequence encodes the O-methyltransferase (Mi-OMTS) protein of SEQ ID No.3.

3. The host cell according to claim 1, wherein the recombinant expression vector is selected from pGEX-4T, pGEX-2T, pGEX-3X, pGEX-5X and pGEX-6P.

4. The host cell according to claim 3, wherein the recombinant expression vector is pGEX-4T.

5. The host cell according to claim 3, wherein the host cell is *Escherichia coli*.

6. The host cell according to claim 1, wherein the host cell is *Escherichia coli*.

7. A process for synthesis of volatile compounds said process comprising the steps of:
 (a) cloning a cDNA molecule comprising a Mi-OMTS nucleotide sequence of SEQ ID No. 2 in a recombinant expression vector;
 (b) transforming the recombinant expression vector of step (a) in *E. coli;*
 (c) expressing the Mi-OMTS nucleotide sequence of SEQ ID No. 2 to produce a Mi-OMTS protein of SEQ ID No. 3 in *E. coli;*
 (d) extracting said Mi-OMTS protein of step (c) by *E. coli* cell lysis;
 (e) carrying out chromatography and filtration of the extracted protein of step (d) to obtain purified protein of molecular weight ranging from 35 kDa to 40 kDa;
 (f) treating the purified protein of step (e) with a substrate and a methyl group donor selected from S-adenosyl methionine (SAM); and
 (g) incubating components of step (f) at a temperature of 25° C.-30° C. and pH of 6 to 8 for 30 min to obtain volatile flavour compounds.

8. The process according to claim 7, where in the substrate in step (f) is selected from furaneol, caffeic acid, catechol and protocatechuic aldehyde.

9. The process according to claim 7, wherein the volatile compounds are selected from mesifuran, ferulic acid, guaiacol and vanillin.

10. The process according to claim 7, wherein the volatile compounds are mesifuran and vanillin.

11. A process for synthesis of volatile compounds said process comprising the steps of:
 (a) expressing a Mi-OMTS protein of SEQ ID No. 3 in *E. coli;*
 (b) extracting the Mi-OMTS protein of step (a) by *E. coli* cell lysis;

(c) carrying out chromatography and filtration of the extracted protein of step (b) to obtain purified protein of molecular weight ranging from 35 kDa to 40 kDa;
(d) treating the purified protein of step (c) with a substrate and a methyl group donor selected from S-adenosyl methionine (SAM); and
(e) incubating components of step (d) at a temperature of 25° C.-30° C. for 30 min to obtain volatile flavour compounds.

12. The process according to claim 11, wherein the volatile compounds are selected from mesifuran, ferulic acid, guaiacol and vanillin.

13. The process according to claim 11, wherein the volatile compounds are mesifuran and vanillin.

14. The process according to claim 11, wherein the substrate in step (d) is selected from furaneol, caffeic acid, catechol and protocatechuic aldehyde.

* * * * *